United States Patent [19]

Järvinen et al.

[11] Patent Number: 5,064,204
[45] Date of Patent: Nov. 12, 1991

[54] ANALYZER SEALING MEMBER

[75] Inventors: Marja-Leena Järvinen; Jouko A. K. Koskinen, both of Helsinki, Finland

[73] Assignee: Outokumpu Oy, Helsinki, Finland

[21] Appl. No.: 644,403

[22] Filed: Jan. 22, 1991

Related U.S. Application Data

[63] Continuation of Ser. No. 368,657, Jun. 20, 1989, abandoned.

[30] Foreign Application Priority Data

Jun. 22, 1988 [FI] Finland .................... 883013

[51] Int. Cl.$^5$ .............................................. F16J 15/447
[52] U.S. Cl. ........................................ 277/53; 313/619; 356/311; 378/44
[58] Field of Search ................ 277/53; 313/634, 619; 356/311, 313, 314; 378/44, 45, 208

[56] References Cited

U.S. PATENT DOCUMENTS

| 2,878,048 | 3/1959 | Peterson | 277/53 X |
|---|---|---|---|
| 3,013,824 | 12/1961 | Wilson | 277/53 |
| 3,876,305 | 4/1975 | Gough et al. | 356/314 |
| 4,330,133 | 5/1982 | Palfreyman et al. | 277/53 X |
| 4,401,893 | 8/1983 | Dehuysser | 356/239 X |
| 4,484,754 | 11/1984 | Ballard | 277/53 |
| 4,544,270 | 10/1985 | Berstermann et al. | 356/313 |
| 4,572,517 | 2/1986 | Rockwood et al. | 277/53 |
| 4,641,968 | 2/1987 | Grandy | 356/313 |
| 4,743,034 | 5/1988 | Kakabaker et al. | 277/53 |
| 4,842,287 | 6/1989 | Weeks | 277/53 |

FOREIGN PATENT DOCUMENTS

| 174374 | 3/1986 | European Pat. Off. . |
|---|---|---|
| 2833324 | 2/1980 | Fed. Rep. of Germany . |
| 14308 | 3/1930 | U.S.S.R. . |
| 352062 | 9/1972 | U.S.S.R. . |
| 1182224 | 9/1985 | U.S.S.R. . |
| 1490991 | 11/1977 | United Kingdom . |

OTHER PUBLICATIONS

H. Hugo Bucher: "Industrial Sealing Technology", publ. 1979, pp. 382, 391–395.

Primary Examiner—Thomas B. Will
Assistant Examiner—Scott W. Cummings
Attorney, Agent, or Firm—Dellett, Smith-Hill and Bedell

[57] ABSTRACT

A sealing member used in a portable or on-line analyzer, to achieve a tight seal between a sample and the analyzer in order to perform the analysis in a desired gas atmosphere. The sealing member is a semi-labyrinth sealing member manufactured of metal, elastic material or ceramic material.

11 Claims, 1 Drawing Sheet

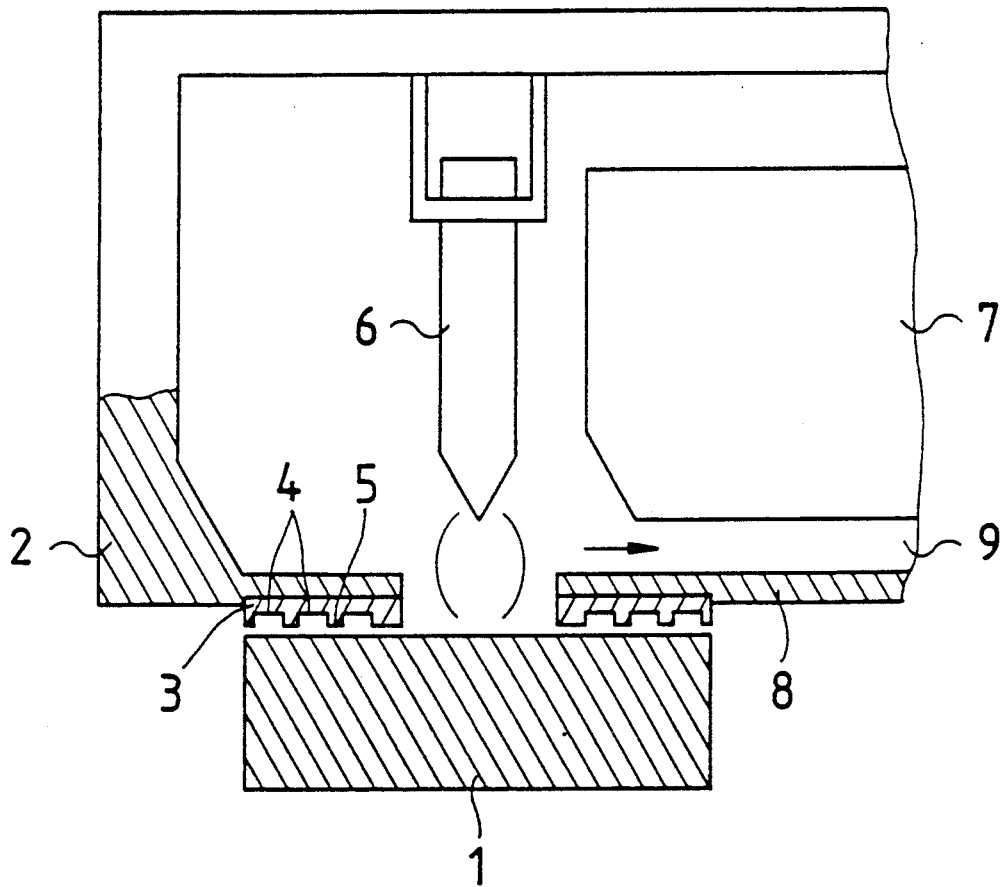

ANALYZER SEALING MEMBER

This is a continuation of application Ser. No. 07/368,657 filed June 20, 1989 and now abandoned.

BACKGROUND OF THE INVENTION

This invention relates to a sealing member used in an analyzer, particularly in a portable analyzer or an on-line analyzer, by which sealing member it is possible to achieve a tight seal between a stationary sample and the analyzer in order to perform the analysis in a desired gas atmosphere.

When analyzing a sample of conductive material, such as metal, using optical emission analysis, an electric discharge is created between the sample and the electrode of the probe. In an apparatus that uses optical emission analysis, the sample is pressed against the probe. In the thus-formed measuring chamber, an argon atmosphere is normally used during the measurement. Any oxygen that is present as an impurity in the chamber atmosphere impairs the accuracy of the result of the analysis. A metal-to-metal pressure contact exists between the analyzer probe and the sample. This kind of a contact can provide a satisfactory seal in the case of a stationary analyzer, but, for example in a portable or on-line analyzer, it has not been possible to create a satisfactory seal by pressure contact between the sample and the probe.

Attempts have been made to improve the seal between a sample and the probe of an optical emission analyzer by, for example, positioning a silicon mat between the sample and the probe. Further, in the apparatus according to the DE patent application 2833324 an elastic O-ring is used in the seal. The use of a sealing ring is also described in the EP patent application 174374 and in the GB patent 1490991. However, the one-part elastic sealing ring described in the references mentioned above does not necessarily give a sufficient seal, because the gas components in the external atmosphere, as oxygen, can be absorbed through this kind of seal. In a stationary optical emission analyzer designed for laboratory use the seal can also be manufactured of a ceramic material, when the electrical connection between the probe and the sample is achieved otherwise than by pressure contact between the probe and the seal. This arrangement is, however, inconvenient for a portable or on-line analyzer.

SUMMARY OF THE INVENTION

The object of the present invention is to avoid some of the drawbacks of the prior art and to realize an improved seal, particularly between the probe and the sample in a portable or on-line analyzer, in which seal a body consisting of many parts is used as the sealing medium.

According to the invention the interface between the probe of an analyzer and a sample is provided with increased resistance to flow of impurity, such as an oxygen-containing gas outside of the measuring chamber of an analyzer, by using a semi-labyrinth seal.

The semi-labyrinth seal is a so-called non-contact seal in which teeth project from one surface toward a non-toothed surface and is generally used in the treatment of liquids around rotating shafts. The semi-labyrinth seal advantageously provides several consecutive choke points, across each of which is created a pressure difference owing to the flowing medium. Between two consecutive choke points there is a labyrinth chamber. The choke point is formed by a very thin sealing margin which reaches close to the surface of the opposed body.

In the semi-labyrinth seal the labyrinth chamber advantageously has such a form that the kinetic energy of the flow from the choke point is removed by being converted into thermal energy. At the following choke point a wholly new flow is created and there is a new pressure drop which represents the kinetic energy of this new flow. If the distance between the choke points of the semi-labyrinth seal is too small, it is possible that the flow due to a single pressure drop can spurt through several choke points.

BRIEF DESCRIPTION OF THE DRAWING

In the following, the invention is explained in more detail with reference to the appended drawing which is a schematic view of one preferred embodiment of the invention applied to an optical emission analyzer.

DETAILED DESCRIPTION

According to the figure, the probe 2 of an optical emission analyzer is provided with a sealing member 3 so that when the sample 1 and is presented to the probe 2 a semi-labyrinth seal is formed between the sample and the probe. The sealing member 3 forms at least two labyrinth chambers 4 so that the choke point 5 between the labyrinth chambers 4 is in its width at least about 50 percent of the width of the labyrinth chamber 4. The figure also shows an electrode 6 in the measuring chamber. An electric discharge is formed between the electrode 6 and the sample 1. The discharge evaporates some material off the sample surface and forms a plasma, from which a distinctive spectrum for each element is conducted through the slot 9 between the collimator 7 and the wall 8 of the probe for further treatment.

The sealing member according to the invention is advantageously manufactured of metal, such as brass or stainless steel, but the sealing member according to the invention can also be manufactured, for example, of an elastic material, such as rubber, or of a ceramic material.

The sealing member according to the invention may be used with advantage between the sample and the measuring chamber of an optical emission analyzer, but the sealing member can also be used in analyzers of other types in which an especially tight seal is required between the stationary sample and the measuring chamber. These kinds of analyzers are, for example, portable X-ray analyzers. Similarly, the analyzer seal created by a sealing member according to the invention can be used in glow discharge lamps.

We claim:

1. An improved analyzer comprising a probe body that defines a measurement chamber for receiving a gas, said probe body being surrounded by an external atmosphere, and an aperture to which a sample is presented for analysis in an atmosphere of the gas that is received in the measurement, chamber, and a sealing member for establishing a substantially gas-tight seal between the probe body and the sample which acts to separate the gas in said measurement chamber from the external atmosphere, wherein the improvement resides in that the sealing member is a semi-labyrinth sealing member.

2. An analyzer according to claim 1, wherein the sealing member is made of metal.

3. An analyzer according to claim 2, wherein the sealing member is made of brass.

4. An analyzer according to claim 2, wherein the sealing member is made of stainless steel.

5. An analyzer according to claim 1, wherein the sealing member is made of elastomeric material.

6. An analyzer according to claim 5, wherein the sealing member is made of rubber.

7. An analyzer according to claim 1, wherein the sealing member is made of ceramic material.

8. An analyzer according to claim 1, wherein the semi-labyrinth sealing member defines at least one labyrinth chamber between two adjacent choke points, and the width of each choke point is at least about 50 percent of the width of the labyrinth chamber.

9. An improved optical emission analyzer comprising a probe body that defines a measurement chamber for receiving a gas, said probe body being surrounded by an external atmosphere, and a aperture to which a sample is presented for optical emission analysis in an atmosphere of the gas that is received in the measurement chamber, and a sealing member for establishing a substantially gas-tight seal between the probe body and the sample which acts to separate the gas in said measurement chamber from the external atmosphere, wherein the improvement resides in that the sealing member is a semi-labyrinth sealing member.

10. An improved X-ray analyzer comprising a probe body that defines a measurement chamber for receiving a gas, said probe body being surrounded by an external atmosphere, and an aperture to which a sample is presented for X-ray analysis in an atmosphere of the gas that is received in the measurement chamber, and a sealing member for establishing a substantially gas-tight seal between the probe body and the sample which acts to separate the gas in said measurement chamber from the external atmosphere, wherein the improvement resides in that the sealing member is a semi-labyrinth sealing member.

11. An improved glow discharge lamp comprising a first body that defines a chamber for receiving a gas, said first body being surrounded by an external atmosphere, and an aperture through which a second body is exposed to the gas that is received in the chamber, and a sealing member for establishing a substantially gas-tight seal between the first body and the second body which acts to separate the gas in said chamber from the external atmosphere, wherein the improvement resides in that the sealing member is a semi-labyrinth sealing member.

* * * * *